US010961506B2

(12) United States Patent
Kokaji

(10) Patent No.: US 10,961,506 B2
(45) Date of Patent: Mar. 30, 2021

(54) SOLUBLE ANTIBODY COMPLEXES FOR T CELL OR NK CELL ACTIVATION AND EXPANSION

(71) Applicant: StemCell Technologies Inc., Vancouver (CA)

(72) Inventor: Andy Isamu Kokaji, Vancouver (CA)

(73) Assignee: STEMCELL Technologies Inc., Vancouver (CA)

( * ) Notice: Subject to any disclaimer, the term of this patent is extended or adjusted under 35 U.S.C. 154(b) by 1008 days.

(21) Appl. No.: 14/844,717

(22) Filed: Sep. 3, 2015

(65) Prior Publication Data

US 2016/0068811 A1    Mar. 10, 2016

Related U.S. Application Data

(60) Provisional application No. 62/045,591, filed on Sep. 4, 2014.

(51) Int. Cl.
*C12N 5/0783* (2010.01)
*C07K 14/725* (2006.01)
*C07K 14/705* (2006.01)

(52) U.S. Cl.
CPC ......... *C12N 5/0646* (2013.01); *C12N 5/0636* (2013.01); *C12N 2501/51* (2013.01); *C12N 2501/515* (2013.01); *C12N 2501/53* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,868,109 A | 9/1989 | Lansdorp | |
| 6,352,694 B1 | 3/2002 | June et al. | |
| 7,135,340 B2 | 11/2006 | Wognum | |
| 7,592,431 B2 | 9/2009 | Har-Noy | |
| 8,012,750 B2 | 9/2011 | Har-Noy | |
| 2007/0036783 A1 | 2/2007 | Humeau et al. | |
| 2014/0087462 A1 | 3/2014 | Scheffold et al. | |

FOREIGN PATENT DOCUMENTS

| | | |
|---|---|---|
| EP | 0173494 A2 | 3/1986 |
| EP | 0171496 B1 | 5/1993 |
| EP | 239400 B1 | 8/1994 |
| GB | 2177096 B | 5/1989 |
| WO | WO2004/065590 A2 | 8/2004 |

OTHER PUBLICATIONS

Le Gall et al (FEBS Letters, 1999, 164-168) (Year: 1999).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Holliger and Hudson (Nature Biotech. 2005, 23: 1126-1136) (Year: 2005).*
Invitrogen (2020) (Year: 2020).*
BD (2020) (Year: 2020).*
Galea-Lauri et al (J. Immunol. 1999, 163: 62-70) (Year: 1999).*
Cell Sciences (2019) (Year: 2019).*
Reinhold et al (Int. Immunol. 1999 11(5): 707-718) (Year: 1999).*
BioCell (2020) (Year: 2020).*
BioLegend (2013) (Year: 2013).*
Beckman Coulter (2005) (Year: 2005).*
ThermoFisher Scientific (2020) (Year: 2020).*
BD Biosciences (2020) (Year: 2020).*
Wikimedia Commons (2018) (Year: 2018).*
Baroja, M. L. et al., "The Anti-T Cell Monoclonal Antibody 9.3 (Anti-CD28) Provides a Helper Signal and Bypasses the Need for Accessory Cells in T Cell Activation with Immobilized Anti-CD3 and Mitogens", Cellular Immunology 120: 205-217 (1989).
Dixon, J. F. P. et al., "Activation of Human T Lymphocytes by Crosslinking of Anti-CD3 Monoclonal Antibodies", Journal of Leukocyte Biology 46: 214-220 (1989).
Kruisbeek, A. M. et al., "Proliferative Assays for T Cell Function", Current Protocols in Immunology 3.12.1-3.12.20 (2004).
Morrison et al., "Chimeric human antibody molecules: Mouse antigen-binding domains with human constant region domains", Proc. Natl Acad. Sci. USA, vol. 81, p. 6851-6855 (1984).
Smith-Garvin, J. E. et al., "T Cell Activation", T Cell Activation. Annual Review of Immunology 27: 591-619 (2009).
Takeda, S. et al., "Construction of chimeric processed immunoglobulin genes containing mouse variable and human constant region sequences", Nature, vol. 314, p. 452-454 (1985).
Cho et al. "Expansion and activation of natural killer cells for cancer immunotherapy", Korean Journal of Laboratory Medicine, vol. 29, No. 2, Apr. 2009, p. 89-96.
Geppert T.D. et al. "Activation of human T4 cells by cross-linking class I MHC molecules", J Immunol, vol. 140, No. 11, Apr. 1, 1988, p. 2155-2164.
Lansdorp et al. "Cyclic tetramolecular complexes of monoclonal antibodies: a new type of cross-linking reagent", European Journal of Immunology, vol. 16, No. 6, Jun. 1986, p. 679-683.
Wacholtz et al. "Patterns of costimulation of T cell clones by cross-linking CD3, CD4/CD8 and class I MHC molecules", The Journal of Immunology, Jun. 15, 1989, p. 4201-4212.

(Continued)

*Primary Examiner* — Michael Szperka
*Assistant Examiner* — Marianne DiBrino
(74) *Attorney, Agent, or Firm* — Bereskin & Parr LLP/S.E.N.C.R.L., s.r.l.; Micheline Gravelle

(57) ABSTRACT

This disclosure provides compositions and methods for the activation and expansion of human T cells or NK cells using soluble monospecific antibody complexes.

5 Claims, 6 Drawing Sheets

(56) References Cited

OTHER PUBLICATIONS

Peters et al. "Isolation of Subsets of Immune Cells", Methods in Molecular Biology, vol. 302, 2005, p. 95-115.
Trickett et al. "T cell stimulation and expansion using anti-CD3/CD28 beads", Journal of Immunological Methods, vol. 275, No. 1-2, Apr. 1, 2003, p. 251-255.

* cited by examiner

FIGURE 2

| Sample # | Well pre-treatment | T cell activation stimulus (TAC or Dynabeads) | Final [TAC] (ug/mL) | Dynabead to Cell Ratio | %CD8+ Divided (day 3) | %CD4+ Divided (day 3) | Total Viable Cells (day 6) |
|---|---|---|---|---|---|---|---|
| 1 | - | Unstimulated | - | - | 0.74 | 1.06 | 3.17E+04 |
| 2 | - | CD3 | 0.5 | - | 11.67 | 7.4 | 7.71E+04 |
| 3 | - | CD3 + CD28.2 | 0.5 | - | 78.09 | 66.26 | 1.09E+06 |
| 4 | - | CD3 + CD28.2 + CD2 | 0.5 | - | 71.88 | 55.28 | 1.03E+06 |
| 5 | - | CD3/CD28 Dynabeads | - | 3:1 | 90.08 | 81.01 | 1.51E+06 |
| 6 | 1% HSA | Unstimulated | - | - | 0.87 | 1.01 | 5.45E+03 |
| 7 | 1% HSA | CD3 | 0.5 | - | 1.3 | 1.07 | 3.83E+02 |
| 8 | 1% HSA | CD3 + CD28.2 | 0.5 | - | 39.68 | 33.24 | 2.46E+05 |
| 9 | 1% HSA | CD3 + CD28.2 + CD2 | 0.5 | - | 60.56 | 47.42 | 9.63E+05 |
| 10 | 1% HSA | CD3/CD28 Dynabeads | - | 3:1 | 90.98 | 83.53 | 1.11E+06 |

FIGURE 3

| Sample # | T cell activation stimulus (TAC or Dynabeads) | Final [TAC] (ug/mL) | Dynabead to Cell Ratio | %CD4+ IL-2+ | %CD4+ IFNg+ | %CD8+ IL-2+ | %CD8+ IFNg+ |
|---|---|---|---|---|---|---|---|
| 1 | CD3 | 0.5 | - | 0.02 | 0.15 | 0.1 | 0.34 |
| 2 | CD3 + CD28 | 0.5 | - | 2.4 | 0.5 | 2.45 | 1 |
| 3 | CD3 + CD28 + CD2 | 0.5 | - | 3.81 | 0.86 | 3.48 | 1.23 |
| 4 | CD3/CD28 Dynabeads | - | 3:1 | 3.87 | 1.95 | 4.04 | 3.43 |

SOLUBLE ANTIBODY COMPLEXES FOR T CELL OR NK CELL ACTIVATION AND EXPANSION

RELATED APPLICATIONS

This application claims priority to U.S. Provisional Patent Application No. 62/045,591 filed Sep. 4, 2014, the contents of which are incorporated by reference herein in their entirety.

FIELD

The disclosure relates to methods and compositions of soluble monospecific antibody complexes for human T cell or NK cell activation and expansion.

BACKGROUND

Host tolerance and adaptive immunity are complex and critical components of human health. T lymphocytes are comprised of various subsets including regulatory T cells, which play a major role in the maintenance of host tolerance; effector subsets such as CD4+ T helper cells and CD8+ cytotoxic T cells that carry out immune responses according to the environmental stimuli.

Methods for the growth and propagation of T cells in vitro have been based upon a number of different approaches. In some circumstances. T cells are activated and expanded by use of accessory cells and exogenous growth factors, such as antigen presenting cells and IL-2. This requires the presence and replenishment of accessory cells and growth factors during the course of T cell activation and/or expansion.

Alternatively, reagents used for the activation and expansion of T cells consist of a combination of direct or indirect immobilization of anti-CD3 antibodies, on a solid phase surface such as a plate or on a magnetic bead. In addition to the primary T cell activation signal provided by the immobilized anti-CD3 antibodies, a secondary co-stimulation signal provided by anti-CD28 antibodies is required. Exogenous growth factors or cytokines such as IL-2 can also be added to enhance T cell proliferation.

Antibodies against CD3 are a critical component in many polyclonal T cell stimulation protocols. It was first demonstrated by Dixon at al., that immobilized anti-CD3 could mediate human T cell activation and expansion in the absence of cognate antigen recognition by the T cell receptor. Anti-CD3 initiates the activation and proliferation signaling cascade by crosslinking the components of the T cell receptor complex on the surface of T cells; thus their requirement for immobilization. It was subsequently shown by Baroja et al., that a second signal from either an immobilized or soluble anti-CD28 stimuli was required for full T cell activation in combination with immobilized anti-CD3. Additional costimulatory signals provided through adhesion ligands such as CD2, LFA-1 and other TNF family members such as CD137 (4-1BB) can provide additional proliferative or survival signals to the T cells (Smith-Garvin et. al).

Commercial products for T cell activation using tissue culture plates coated with immobilized anti-CD3 antibodies are available from Corning (BioCoat™ T cell activation plates. Cat #354725) and are widely prepared by researchers using standard methods known to those familiar with the art. Soluble anti-CD28 antibodies can be added exogenously to provide the costimulatory signal necessary to initiate T cell activation and proliferation (Kruisbeek et, al.).

U.S. Pat. No. 6,352,694, describes a method for T cell activation and expansion using anti-CD3 and anti-CD28 antibodies immobilized on a 4.5 um diameter magnetic particle.

U.S. Pat. No. 8,012,750B2 describes a biodegradable device for activating T cells. Similar to the previous disclosure, the method uses a biodegradable microsphere indirectly coated with antibodies capable of binding to and activating T cells.

U.S. patent application Ser. No. 14/035,089 describes the use of a flexible nanomatrix with immobilized anti-CD3 and/or anti-CD28 to provide a activation signal to T cells. They disclose a dextran matrix between 1-500 nm in size that functions as a flexible scaffold that can mold onto the surface of a T cell that has immobilized T cell activation antibodies.

Unlike immobilized antibodies, soluble antibody complexes may provide a gentler activation signal to T cells. U.S. publication no. US 2007/0036783 describes the use of soluble bispecific tetrameric antibody complexes (TAC) composed of one anti-CD3 antibody in complex with a second antibody against CD28 that can initiate T cell activation and expansion. They claim that this approach provides a gentler stimulus resulting in lower activation induced cell death compared to immobilized antibody methods. The inventors of this application did not fully demonstrate that the tetrameric antibody complexes were in fact soluble and not adsorbed onto the culture plastic during the course of stimulation. In addition, the inventors specifically state the use of bi-specific tetrameric antibody complexes are involved in the activation and expansion of the stimulated T cells.

SUMMARY

The present inventor has developed a method for the use of soluble monospecific tetrameric antibody complexes for the activation and expansion of primary human T cells or NK cells in vitro. In particular, the inventor has determined that using soluble monospecific tetrameric antibody complexes results in a greater activation of T cells as compared to using bispecific tetrameric antibody complexes. The inventor has also determined that using soluble monospecific tetrameric antibody complexes results in an improvement in NK cell activation compared to NK cells cultured in the absence of soluble monospecific tetrameric antibody complexes.

Soluble monospecific TAC have the advantage over immobilized antibody methods since large magnetic particles do not need to be removed following expansion and the cells can be washed to remove any unbound soluble TAC complexes; nor is there a requirement for specialized antibody coated plates or matrices.

Accordingly, the present disclosure relates to a method of activating T cells or NK cells comprising culturing a sample containing T cells or NK cells with a composition comprising at least one soluble monospecific complex, wherein each soluble monospecific complex comprises two binding proteins which are linked and bind to the same antigen on the T cells or NK cells.

In one embodiment, the composition comprises at least two different monospecific antibody complexes, wherein one monospecific antibody complex binds to a first antigen on the T cells or NK cells and the other monospecific antibody complex binds to a second antigen on the T cells or NK cells. Optionally, the composition comprises at least three different monospecific antibody complexes, wherein the first monospecific antibody complex binds to a first antigen, the second monospecific antibody complex binds to a second antigen and the third monospecific antibody complex binds to a third antigen on the T cells or NK cells.

In one embodiment, the binding proteins described herein that bind to antigens on T cells or NK cells are antibodies or fragments thereof. In one embodiment, the soluble monospecific complexes are tetrameric antibody complexes (TACO. In one embodiment, the TACs are composed of two antibodies from one species bound by two antibody molecules from a second species that bind to the Fc portion of the antibodies of the first animal species.

In one embodiment, the methods described herein are for activating T cells. In one embodiment, the method comprise culturing a sample containing T cells with a composition comprising one monospecific antibody complex that binds to a first antigen on the T cells and another monospecific antibody complex that binds to a second antigen on the T cells. In one embodiment, the first antigen is selected from CD3, CD28, CD2, CD7, CD11a, CD26, CD27, CD30L, CD40L, OX-40, ICOS, GITR, CD137, and HLA-DR and the second antigen is a different antigen selected from CD3, CD28, CD2, CD7, CD11a, CD26, CD27, CD30L, CD40L, OX-40, ICOS, GITR, CD137, and HLA-DR. In one embodiment, the first antigen is CD3. In one embodiment, the second antigen is CD28. In one embodiment, the third antigen is CD2.

In one embodiment, the T cell activation is enhanced T cell proliferation, enhanced cytokine production and/or enhanced T cell expression.

In one embodiment, the present disclosure describes the use of soluble monospecific tetrameric antibody complexes that target human CD3, CD28 and CD2 to induce optimal in vitro polyclonal activation and expansion of human T cells. In such an embodiment, the composition comprises three different soluble monospecific complexes that target CD3, CD28 and CD2.

In another embodiment, the methods described herein are for activating NK cells. In one embodiment, the method comprises culturing a sample containing NK cells with a composition comprising one monospecific antibody complex that binds to a first antigen on the NK cells and another monospecific antibody complex that binds to a second antigen on the NK cells. In one embodiment, the first antigen is selected from CD335, CD2, NKG2D, NKp44, NKp30, CD16, LFA-1 and CD27 and the second antigen is a different antigen selected from CD335, CD2, NKG2D, NKp44, NKp30, CD16, LFA-1 and CD27. In one embodiment, the first antigen is CD335. In one embodiment, the second antigen is CD2.

In one embodiment, the NK cell activation is enhanced NK cell proliferation, enhanced cytokine production and/or enhanced NK cell expression.

In one embodiment, the present disclosure describes the use of soluble monospecific tetrameric antibody complexes that target human CD335 and CD2 to induce in vitro activation and expansion of human NK cells. In such an embodiment, the composition comprises two different soluble monospecific complexes that target CD335 and CD2.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

FIG. 2 shows the results of T cell activation and proliferation using soluble monospecific TAG compositions and Dynabead® Human T-Activator CD3/CD28 beads using untreated or blocked tissue culture plates.

FIG. 3 shows the results of a short term intracellular cytokine production assay following stimulation with soluble monospecific TAC compositions or Dynabead® Human T-Activator CD3/CD28 beads.

DETAILED DESCRIPTION

Figure 1:
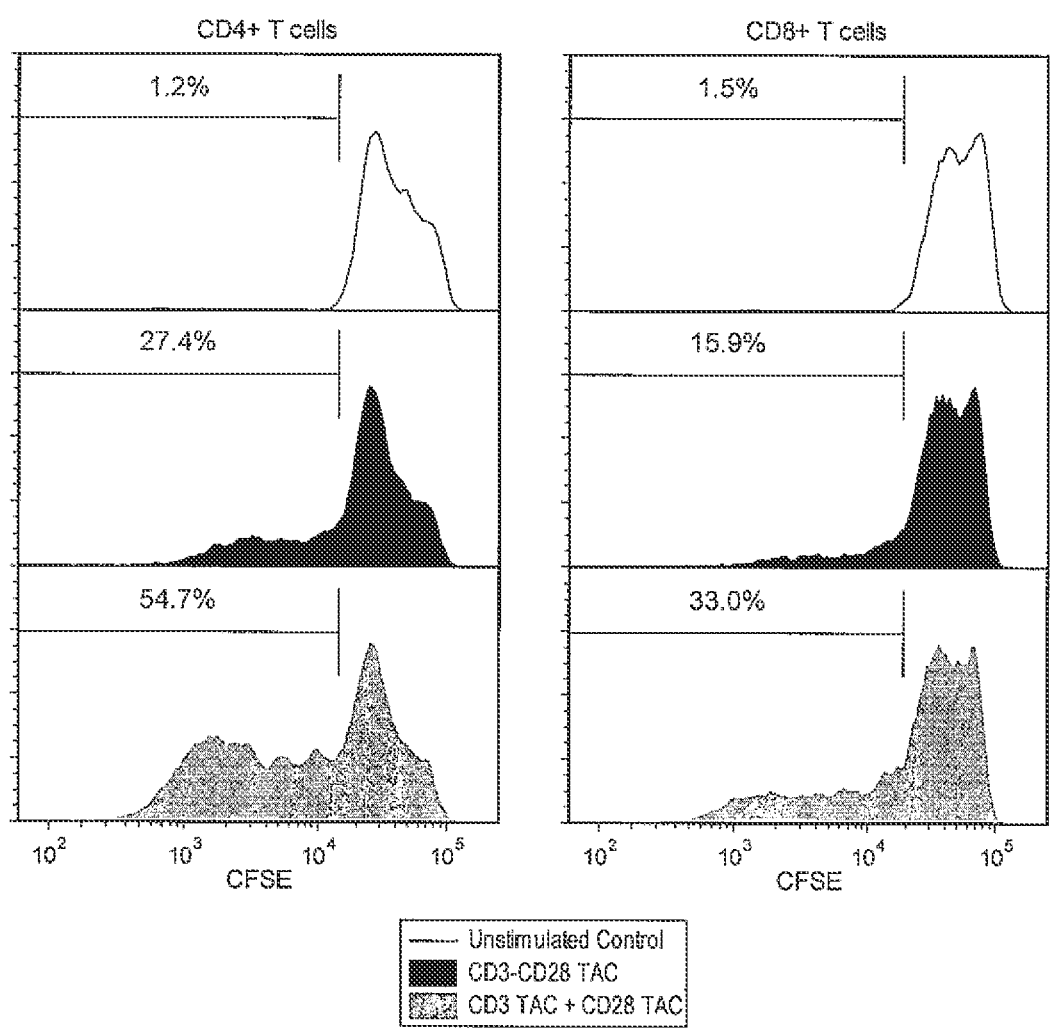
FIG. 1 shows the results of human T cell proliferation as assessed by CFSE dye dilution using a mixture of monospecific TAG specific for CD3 or CD28, or using a mixture of bi-specific TAG against CD3 and CD28 following 7 days of culture.

The present disclosure provides a method of activating and expanding human T cells or Natural Killer (NK) cells in vitro using a monospecific complex such as a tetrameric antibody complex.

Accordingly, in one embodiment, the present disclosure provides a method of activating T cells comprising culturing a sample containing T cells with a composition comprising at least one soluble monospecific complex, wherein each soluble monospecific complex comprises two binding proteins which are linked and bind to the same antigen on the T cells. In one embodiment, the present disclosure also provides a method of activating NK cells comprising culturing a sample containing NK cells with a composition comprising at least one soluble monospecific complex, wherein each soluble monospecific complex comprises two binding proteins which are linked and bind to the same antigen on the NK cells. In one embodiment, the NK cells are cultured in the presence of IL-2 and/or one or more other cytokines such as IL-7 or IL-15. In one embodiment, the T cells or NK cells are human cells.

The term "soluble monospecific complex" as used herein means a complex that comprises two binding proteins that are linked, either directly or indirectly, to each other and bind to the same antigen. The two binding proteins are soluble and not immobilized on a surface, particle or bead. In one embodiment, the binding proteins bind to the same antigen on the cells. In another embodiment, the binding proteins bind to the same antigen on the NK cells.

In one embodiment, the two binding proteins are the same binding protein and bind to the same epitope on the antigen.

The term "bispecific complex" as used herein means a complex that comprises two different binding proteins that are linked, either directly or indirectly, to each other wherein each binding protein binds to a different antigen on the T cells or NK cells.

The term "activating T cells" includes, without limitation, inducing the proliferation of T cells, inducing cytokine production from the T cells and inducing T cell expansion.

The "antigen on the T cells" can be any antigen that activates T cells including, without limitation, CD3, CD28, CD2, CD7, CD11a, CD26, CD27, CD30L, CD40L, OX-40, ICOS, GITR, CD137, and HLA-DR.

The term "activating NK cells" includes, without limitation, inducing the proliferation of NK cells, inducing cytokine production from the NK cells and inducing NK cell expansion.

The "antigen on the NK cells" can be any that activates NK cells including, without limitation, CD335, CD2, NKG2D, NKp44, NKp30, CD16, LFA-1 and CD27.

In a specific embodiment, the binding proteins are antibodies or fragments thereof. Antibody fragments that may be used include Fab, Fab', F(ab)$_2$, scFv and dsFv fragments from recombinant sources and/or produced in transgenic animals. The antibody or fragment may be from any species including mice, rats, rabbits, hamsters and humans. Chimeric antibody derivatives, i.e., antibody molecules that combine a non-human animal variable region and a human constant region are also contemplated within the scope of the invention. Chimeric antibody molecules can include, for example, humanized antibodies which comprise the antigen binding domain from an antibody of a mouse, rat, or other species, with human constant regions. Conventional methods may be used to make chimeric antibodies. (See, for example, Morrison et al.; Takeda et al., Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). The preparation of humanized antibodies is described in EP-B 10 239400. Humanized antibodies can also be commercially produced (Scotgen Limited, 2 Holly Road, Twickenham, Middlesex, Great Britain.). It is expected that chimeric antibodies would be less immunogenic in a human subject than the corresponding non-chimeric antibody. The humanized antibodies can be further stabilized for example as described in WO 00/61635.

Antibodies or fragments thereof that bind to T cell antigens or NK cell antigens are available commercially or may be prepared by one of skill in the art.

In one embodiment, the two antibodies or fragments thereof which bind to the same antigen are linked directly. Direct linking of the antibodies may be prepared by chemically coupling one antibody to the other, for example by using N-succinimidyl-3-(2-pyridyldithio) propionate (SPDP).

In another embodiment, the two antibodies are indirectly linked in the soluble monospecific complex. By "indirectly linked" it is meant that the two antibodies are not directly covalently linked to each other but are attached through a linking moiety such as an immunological complex. In a preferred embodiment, the two antibodies are indirectly linked by preparing a tetrameric antibody complex. A tetrameric antibody complex may be prepared by mixing monoclonal antibodies that bind to the same antigen and are of the same animal species with approximately an equimolar amount of monoclonal antibodies of a second animal species which are directed against the Fc-fragments of the antibodies of the first animal species. The first and second antibody may also be reacted with an about equimolar amount of the F(ab')2 fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

In one embodiment, the composition comprises at least two different monospecific complexes, each binding to a different antigen on the T cells. In one embodiment, the composition comprises at least two different soluble monospecific complexes and each of the at least two different soluble monospecific complexes binds to a different antigen selected from the group consisting of CD3, CD28, CD2, CD7, CD11a, CD26, CD27, CD30L, CD40L, OX-40, ICES, GITR, CD137, and HLA-DR.

In a specific embodiment, one monospecific complex will bind CD3 and the second monospecific complex will bind CD28.

In another embodiment, the composition comprises at least three different soluble monospecific complexes, each binding to one of three different antigens on the T cells. In such embodiment, no two monospecific complexes will bind the same antigen.

In a specific embodiment, the composition comprises three different soluble monospecific complexes, one specific for CD3, a second specific for CD28 and a third specific for CD2.

In a specific embodiment, the activation of T cells in the presence of the soluble monospecific complexes is greater than the activation of T cells using a bispecific complex comprising two different binding proteins or antibodies, each of which binds to a different antigen on the T cells.

The sample containing T cells can be any sample wherein one wishes to activate T cells including, without limitation, whole blood, apheresis samples or peripheral blood mononuclear cells containing T cells, purified primary human T cells or immortalized human T cell lines.

In one embodiment, the composition comprises at least two different monospecific complexes, each binding to a different antigen on the NK cells.

In a specific embodiment, one monospecific complex will bind CD335 and the second monospecific complex will bind CD2.

In another embodiment, the composition comprises at least two different soluble monospecific complexes, each binding to one of two different antigens on the NK cells. In such embodiment, no two monospecific complexes will bind the same antigen. In one embodiment, the composition comprises at least two different soluble monospecific complexes and each of the at least two different soluble monospecific complexes binds to a different antigen selected from the group consisting of CD335, CD2, NKG2D, NKp44, NKp30, CD16, LFA-1 and CD27.

In a specific embodiment, the composition comprises two different soluble monospecific complexes, one specific for CD335, a second specific for CD2. In one embodiment, the composition comprises at least one additional soluble monospecific complex specific for an antigen selected from NKG2D, NKp44, NKp30, CD16, LFA-1 and CD27.

In a specific embodiment, the activation of NK cells in the presence of the soluble monospecific complexes is greater than the activation of NK cells in the absence of the soluble monospecific complexes.

The sample containing NK cells can be any sample wherein one wishes to activate NK cells including, without limitation, whole blood, apheresis samples or peripheral blood mononuclear cells containing NK cells, purified primary human NK cells or immortalized human NK cell lines.

Composition

The present disclosure also includes compositions comprising at least one soluble monospecific complex, wherein the soluble monospecific complex comprises two binding proteins which are linked and bind to the same antigen on the T cells or NK cells.

In another embodiment, the composition comprises two soluble monospecific complexes, wherein one soluble monospecific complex binds to one antigen on the T cells or NK cells and the second soluble monospecific complex binds to a different antigen on the T cells or NK cells.

In another embodiment, the composition comprises three soluble monospecific complexes, wherein each complex binds to a different antigen on the T cells. In a specific embodiment, the antigens are CD3, CD28 and CD2.

In another embodiment, the composition comprises two soluble monospecific complexes, wherein each complex binds to a different antigen on the NK cells. In a specific embodiment, the antigens are CD335 and CD2.

Uses

The present disclosure includes all uses of the activated T cells or NK cells including, without limitation, their use in therapy.

The methods and compositions of the present disclosure may be used to expand T cells or NK cells ex vivo for use in vivo in the therapy of any disease or condition requiring T cells or NK cells including, without limitation, adoptive immunotherapy of cancer, acute or persistent pathogen infection (viral, fungal, bacterial, parasite), modulation of vaccine efficacy, or immune suppression of autoimmune disease or graft versus host disease.

The following non-limiting examples are illustrative of the present disclosure:

Example 1

Monospecific CD3 TAC and CD28 TAC induce greater proliferation in human T cells compared to a mixture of bispecific CD3/CD28 TACs (FIG. 1). CD3/CD28 bispecific TACs were prepared by first mixing equivalent volumes of anti-CD3 and anti-CD28 antibodies. Bispecific TACs were formed upon the addition of an equivalent volume of rat anti-mouse IgG1 The resulting TAC mixture contains 25% monospecific anti-CD3 TACs, 25% monospecific anti-CD28 TACs and 50% bispecific anti-CD3/anti-CD28 TACs (See U.S. Pat. No. 4,868,109 to Lansdorp, which is incorporated herein by reference for a description of tetrameric antibody complexes and methods for preparing same).

A CD3 TAC and CD28 TAG monospecific cocktail was prepared by mixing equivalent volumes of either anti-CD3 or anti-CD28 antibodies with an equivalent volume of rat anti-mouse IgG1. The resulting monospecific TACs were mixed at a 1:1 ratio to prepare a CD3 and CD28 monospecific TAC cocktail composed of 50% anti-CD3 TAG and 50% anti-CD28 TAG.

Human T cells were enriched from fresh human whole blood by negative enrichment using RosetteSep™ (STEMCELL Technologies Inc., Vancouver, Canada). Enriched CD4+ T cells were labelled with a final concentration of 1 µM CFDA-SE. Following labelling, the CFSE labelled T cells were resuspended in XVIVO-15 media (Lonza, Basel, Switzerland).

96-well flat bottomed tissue culture plates were blocked with 1% human serum albumin (HSA) in phosphate buffered saline (PBS) overnight at 4° C. To the 1% HSA blocked wells, CFSE labelled cells were cultured in the presence of 0.5 ug/mL final of either monospecific CD3 and CD28 TACs or with CD3/CD28 bispecific TACs. Exogenous IL-2 was not added to the cultures. The samples were cultured for 7 days in a humidified 37° C. incubator with 5% CO2. Following 7 days of culture, samples assessed by flow cytometry for CFSE dye dilution (an indicator of cell proliferation) and expression of CD4 and CD8.

The results demonstrate that monospecific CD3 and CD28 TACs induce greater proliferation of CD4+ and CD8+ T cells compared to bispecific CD3/CD28 TACs. Unstimulated CD4+ and CD8+ T cells underwent minimal proliferation, 1.2% and 1.5%, respectively. 54.7% of CD4+ T cells stimulated with monospecific TACs proliferated in comparison to 27.4% with bispecific TACs. 33.0% of CD8+ T cells stimulated with monospecific TACs proliferated in comparison to 15.9% with bispecific TACs. The results indicate that monospecific TACs alone are capable of inducing T cell proliferation and that a mixture containing 25% monospecific CD3 and CD28 TACs and 50% bi-specific TACs is less efficient at inducing T cell proliferation as assessed by CFSE dye dilution following 7 days of culture.

Example 2

Soluble monospecific CD2 TAC in combination with CD3 and CD28 TAC induce optimal activation of human T cells (FIG. 2). Monospecific TAC were prepared as described in example 1, Monospecific TAC specific for anti-CD3 were prepared using anti-human CD3. Monospecific anti-CD28 TACs were prepared using anti-human CD28. Monospecific anti-CD2 TACs were prepared using anti-human CD2. CFSE labelled purified human T cells were cultured with various combinations of monospecific TACs or with Dynabead® Human T-Activator CD3/CD28 beads in 96-well plates left untreated or blocked with 1% HSA. The combinatorial effect of: i) anti-CD3 TAC alone, ii) anti-CD3 TAC and anti-CD28 TAC or iii) anti-CD3 TAC, anti-CD28 TAG and anti-CD2 TAC on T cell proliferation (CFSE dye dilution) was assessed by flow cytometry after 3 days of culture in XVIVO-15 medium. Viable cell counts were performed using a Guava ViaCount assay on days 6 of culture.

Prior to culturing the cells, the wells of 96-well tissue culture plates were either left untreated or blocked with 1% HSA in PBS overnight at 4 C. Wells were washed with PBS prior to culturing the cells. The HSA will prevent immobilization of antibody complexes to the tissue culture plastic ensuring that stimulation is mediated by soluble TAG in suspension.

Dynabead® Human T-Activator CD3/CD28 beads (samples #5 and #10) are not affected by the well pretreatment and induce high levels of both CD4+ and CD8+ T cell proliferation. Total viable cells on day 6 are similar between the plate treatments when Dynabeads® are used for T cell expansion. CD3 TAG alone is not sufficient to induce T cell expansion (Samples #2 and #6); whereas, the combination of CD3 and CD28 monospecific TAG can induce high levels of T cell proliferation when the wells are left untreated (Sample #3). When CD3 and CD28 TAG are used in 1% HSA blocked wells (Sample #8), proliferation of T cells is significantly reduced with total viable cells on day 6 reduced from 1.09E6 to 2.46E5 cells when compared to the untreated wells with the same stimulus. In contrast, the combination of CD3, CD28 and CD2 monospecific TAG was minimally affected by blocking of the well with HSA (Samples #4 and #9) similar to the Dynabead® Human T-Activator CD3/CD28 beads. Taken together, these data suggest that plate immobilization of CD3 and CD28 monospecific TAG influences their effectiveness at activating T cells. However, if the combination of CD3, CD28 and CD2 monospecific TAC are used to stimulate T cells, this occurs independent of plate immobilization and the monospecific TAC function in a soluble manner. Dynabead® Human T-Activator CD3/CD28 beads are also unaffected by the plate pre-treatment as the anti-CD3 and CD28 antibodies are immobilized to the bead surface.

Example 3

Soluble monospecific CD3, CD28 and CD2 TAC can induce cytokine production by T cells (FIG. 3). RosetteSep™ enriched human T cells were cultured for 4 hours in the presence of various combinations of soluble monospecific TAC constructs or Dynabead® Human T-Activator CD3/CD28 beads (FIG. 3). Brefeidin A was added to the cultures to allow for intracellular cytokine accumulation and assessment by flow cytometry following culture. Cultures were harvested and stained for cell surface markers and intracellular cytokines following fixation and permeabilization.

The results demonstrate that CD3 TAC alone do not induce either IL-2 or IFNγ cytokine production in the T cells following 4 hours of stimulation (Sample #1). The combination of CD3 and CD28 TAG to induce 2.4% and 2.45% of the CD4+ and CD8+ T cells to produce IL-2, respectively (Sample #2). The CD3 and CD28 TAC also induced 0.5% of the CD4-T cells and 1.0% of the CD8+ T cells to produce IFNγ. The combination of CD3, CD28 and CD2 monospecific TAC induced higher levels of IL-2 and IFNγ production by the T cells as compared to CD3 and CD28 TAC alone (Sample #3). Dynabead® Human T-Activator CD3/CD28 beads induced similar levels of IL-2 as the combination of CD3, CD28 and CD2 but induced higher levels of IFNγ (Sample #4). Taken together, these results demonstrate that the combination of CD3, CD28 and CD2 monospecific TAC can induce higher levels of cytokine production by CD4+ and CD8+ T cells compared to CD3 and CD28 TAC alone; while Dynabead® Human T-Activator CD3/CD28 beads induce higher levels of IFNγ. IL-2 aids in the induction of T cell proliferation and differentiation whereas IFNγ is an effector cytokine involved in inducing an anti-viral immune response.

Example 4

Figure 4:
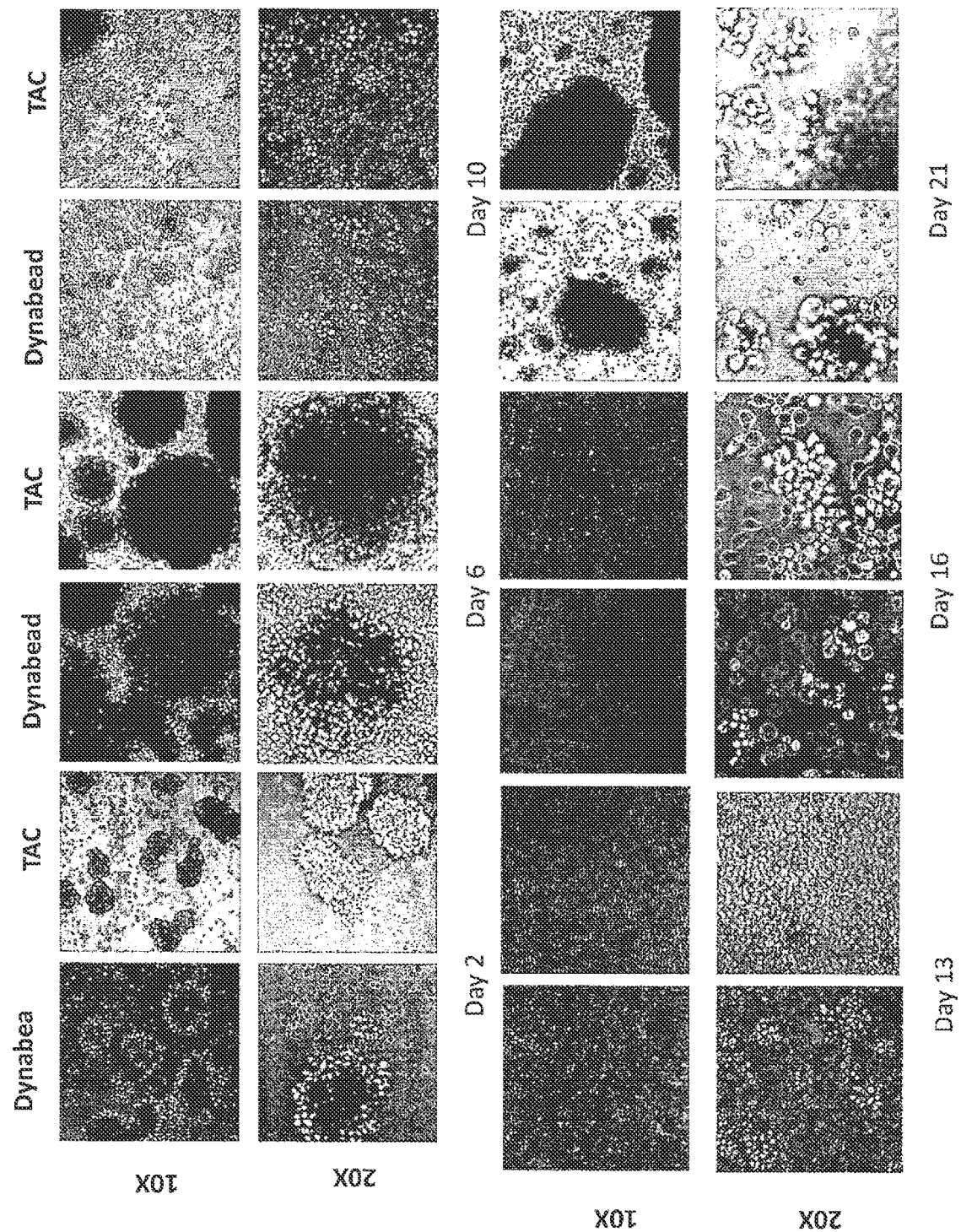
FIG. 4 shows representative images of T cells expanded using soluble monospecific CD3, CD28 and CD2 TAC or Dynabead® Human T-Activator CD3/CD28 beads over the course of 21 days.

Representative images (10× and 20× magnification) of CD3, CD28 and CD2 monospecific TAC stimulated T cells compared to Dynabead® Human T-Activator CD3/CD28 beads stimulated T cells over the course of 21 days (FIG. 4). EASYSEP™ cell separation reagent-enriched human T cells were cultured with either Dynabead® Human T-Activator CD3/CD28 beads at a 1:1 bead to cell ratio, or with 0.5 ug/mL final of CD3, CD28 and CD2 monospecific TAC in the presence of 30 U/mL recombinant human IL-2. Cultures were monitored for cell growth and cell concentration was maintained at 0.5-2×10E6 cells/mL. T cells were restimulated on day 7 and 17 of culture with Dynabead® Human T-Activator CD3/CD28 beads or monospecific CD3, CD28 and CD2 TAC.

Dynabead® Human T-Activator CD3/CD28 beads and monospecific CD3, CD28 and CD2 TAC stimulated cultures induce similar characteristics of T cell proliferation and expansion. The 4.5 um beads used in the Dynabead® Human T-Activator CD3/CD28 beads can be clearly seen in the cultures. In contrast to Dynabead® Human T-Activator CD3/CD28 beads, the TAG stimulated cultures do not require the removal of the beads prior to any downstream functional assays as the cell sized beads can interfere with downstream analysis such as flow cytometry.

Example 5

Figure 5:
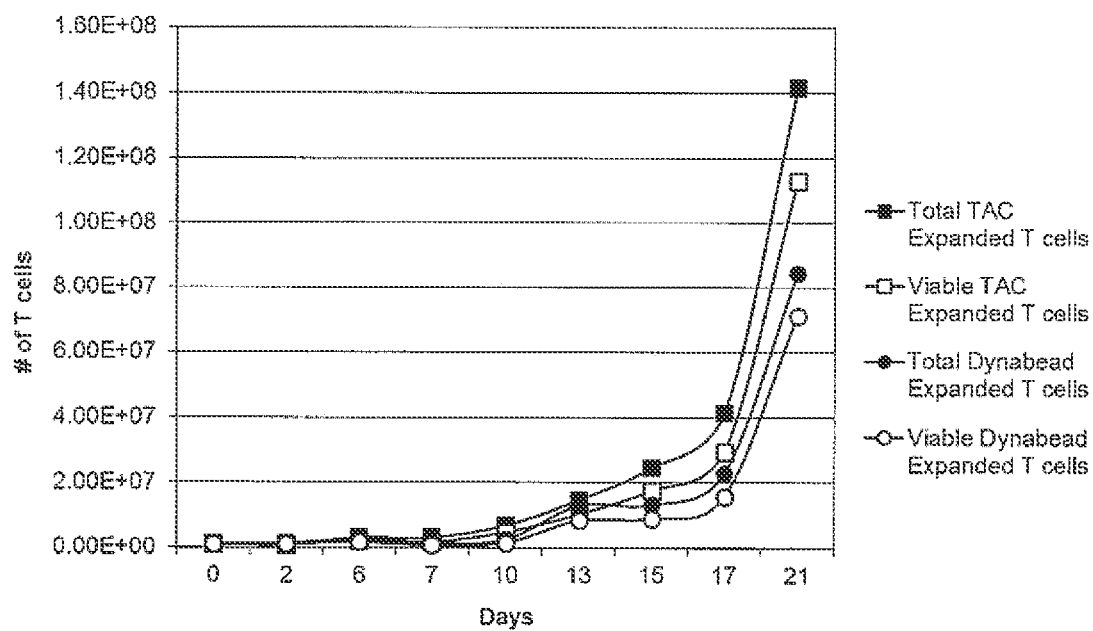
FIG. 5 shows the results of a 21 day T cell expansion using either soluble monospecific CD3, CD28 and 002 TAC or Dynabead® Human T-Activator CD3/CD28 beads.

Long term culture and expansion of human T cells with Dynabead® Human T-Activator CD3/CD28 beads compared to CD3, CD28 and CD2 monospecific TAC (FIG. 5). 1×10E6 EASYSEP™ cell separation reagent-enriched human T cells were cultured with either Dynabead® Human T-Activator CD3/CD28 beads at a 1:1 bead to cell ratio, or with 0.5 ug/mL final of CD3, CD28 and CD2 monospecific TACs in the presence of 30 U/mL recombinant human IL-2. Cultures were monitored for cell growth and cell concentration was maintained at 0.5-2×10E6 cells/mL. T cells were restimulated on day 7 and 17 of culture with Dynabead® Human T-Activator CD3/CD28 beads or monospecific CD3, CD28 and CD2. TAC and media was replaced with fresh media at regular intervals.

On day 0, 1×10E6 EASYSEP™ cell separation reagent-enriched T cells were plated into 24 well tissue culture plates and stimulated with Dynabead® Human T-Activator CD3/CD28 beads or monospecific CD3, CD28 and CD2 TAC. Total cells and viable cells were counted using a haemocytometer with trypan blue at the indicated time points. The results demonstrate that the TAC stimulated cultures resulted in increased total T cell expansion and viable T cells following 21 days of culture.

Example 6

Human NK cells were isolated by negative enrichment using EASYSEP™ Human NK Cell Isolation Kit (STEMCELL Technologies, Cat #17955). Isolated NK cells (CD45+ CD3− CD56+) were cultured in serum- and xeno-free IMMUNOCULT™-XF xeno-free cell expansion media (STEMCELL Technologies, Cat #10981) supplemented with 500 IU/mL of recombinant human IL-2 at a cell density of $1 \times 10^6$ cells/mL. NK cells either received no additional stimulus (no stimulation) or were stimulated with CD335/CD2 monospecific TAC complexes at a final concentration of 0.5 ug/mL of each antibody. On day 3, 6, 8, 10 and 13, total viable cells were counted using a Nucelocounter and NK cell purity was assessed by flow cytometry. Cultures were maintained at ~1×10^6 cells/mL with the addition of fresh IMMUNOCULT™-XF xeno-free cell expansion media supplemented with 500 IU/mL of IL-2.

Figure 6A:
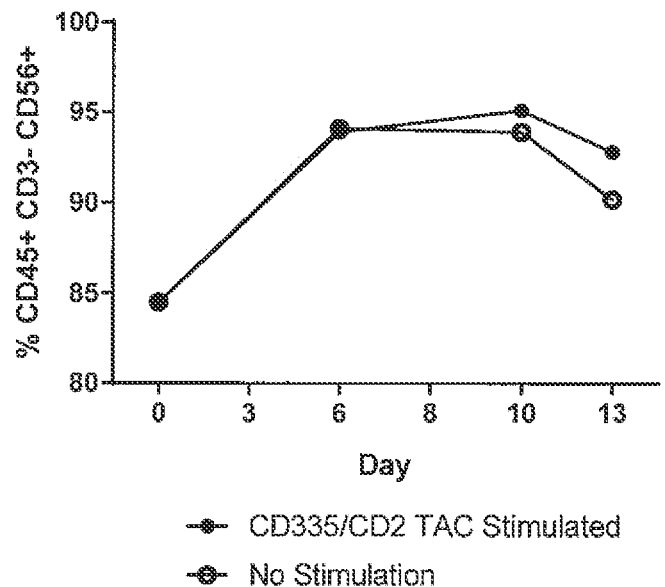
FIG. 6A shows the purity of NK cells maintained in IMMUNOCULT™-XF xeno-free cell expansion media supplemented with IL-2 without stimulation or stimulated with monospecific CD335/CD2 TACs.

As shown in FIG. 6A, NK cells isolated using EASYSEP™ cell separation reagents and maintained in IMMUNOCULT™-XF xeno-free cell expansion media supplemented with IL-2 increased in purity from 84.5% to 94% from day 0 to day 6 irrespective whether they received any additional stimulus. Purity of the NK cells was maintained at a similar level until day 13 of culture.

Figure 6B:
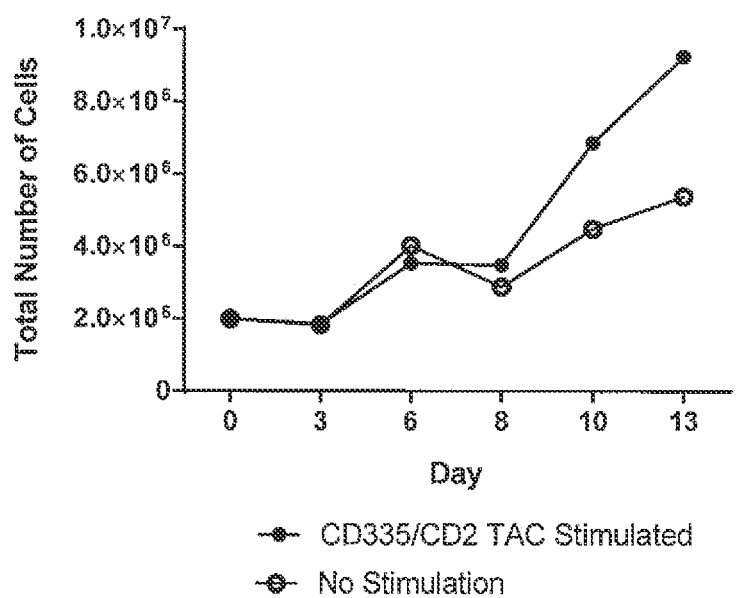
FIG. 6B shows the change in the total number of cells maintained without stimulation or stimulated with monospecific CD335/CD2 TACs. An increase in NK cell activation following stimulation with NKp46 (CD335) and CD2 TAC cocktail in the presence of 500 IU/mL of IL-2 was observed compared to culturing NK cells alone in the presence of 500 IU/mL of IL-2.

As shown in FIG. 6B, NK cells stimulated with monospecific CD335/CD2 TAC complexes increased in cell number between day 8 and day 10 and continuing to day 13 at which point there was a 1.72-fold increase in the number of NK cells in the CD335/CD2 stimulated cultures.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Dixon, J. F. P., Law, J. L, and Favero, J. J. (1989). Activation of Human T Lymphocytes by Crosslinking of Anti-CD3 Monoclonal Antibodies, Journal of Leukocyte Biology 46: 214-220, Baroja, M. L., Lorre, K, Van Vaeck, F., and Ceuppens, J. L. (1989). The Anti-T Cell Monoclonal Antibody 9.3 (Anti-CD28) Provides a Helper Signal and Bypasses the Need for Accessory Cells in T Cell Activation with Immobilized Anti-CD3 and Mitogens. Cellular Immunology 120: 205-217.

Smith-Garvin, J. E., Koretzkey, G. A., and Jordan, M. S. (2009). T Cell Activation. Annual Review of Immunology 27: 591-619.

Kruisbeek, A. M Shevach, E., and Thornton, A. M. (2004). Proliferative Assays for T Cell Function. Current Protocols in Immunology 3.12.1-3.12.20.

Morrison et al., Proc. Natl Acad. Sci, U.S.A. 81, 6851 (1985).

Takeda et al. Nature 314, 452 (1985).

The invention claimed is:

1. A method of activating human T cells comprising culturing a sample containing human T cells with a composition comprising at least one soluble monospecific complex, wherein
   (i) each soluble monospecific complex comprises two antibodies or F(ab')$_2$ fragments thereof which are linked and bind to the same antigen on the human T cells, and
   (ii) the at least one soluble monospecific complex comprises two anti-CD3 antibodies or F(ab')$_2$ fragments thereof that bind a CD3 antigen on the human T cells.

2. The method according to claim 1 wherein the composition further comprises a second soluble monospecific complex that comprises two anti-CD28 antibodies or F(ab')$_2$ fragments thereof that bind to a CD28 antigen on the human T cells.

3. The method according to claim 2 wherein the composition further comprises a third monospecific antibody complex that comprises two anti-CD2 antibodies that bind a CD2 antigen on the human T cells.

4. The method according to claim 1 wherein the soluble monospecific complexes are tetrameric antibody complexes.

5. The method according to claim 4 wherein the tetrameric antibody complexes (TAC) are composed of two antibodies from one species bound by two antibody molecules from a second species that bind to the Fc portion of the antibodies of the first animal species.

* * * * *